US012594179B2

(12) United States Patent
Moore, Sr.

(10) Patent No.: US 12,594,179 B2
(45) Date of Patent: Apr. 7, 2026

(54) BRACE TO COVER ATROPHY IN THE SHOULDER

(71) Applicant: Darrell Wayne Moore, Sr., Glassboro, NJ (US)

(72) Inventor: Darrell Wayne Moore, Sr., Glassboro, NJ (US)

( * ) Notice: Subject to any disclaimer, the term of this patent is extended or adjusted under 35 U.S.C. 154(b) by 386 days.

(21) Appl. No.: 17/248,917

(22) Filed: Feb. 12, 2021

(65) Prior Publication Data

US 2021/0244559 A1      Aug. 12, 2021

Related U.S. Application Data

(60) Provisional application No. 62/975,480, filed on Feb. 12, 2020.

(51) Int. Cl.
*A61F 5/01*      (2006.01)
*A61F 5/32*      (2006.01)
*A61F 5/37*      (2006.01)

(52) U.S. Cl.
CPC .............. *A61F 5/0118* (2013.01); *A61F 5/32* (2013.01); *A61F 5/3723* (2013.01)

(58) Field of Classification Search
CPC .. A61F 5/0118; A61F 5/30; A61F 5/32; A61F 5/3723; A61F 2007/003; A61F 2007/0029; A61F 5/05808; A61F 5/05858; A61F 13/10; A61F 5/34; A61F 5/37; A61F 5/3738; A41D 27/26; A41D 13/0512; A41D 13/00; A41D 13/0012; A41D 13/015; A41D 13/05; A41D 13/055; A41D 13/0556; A41D 13/0562; A41D 3/0568; A41D 13/0575; A41D 13/0151; A41D 13/0153; A63B 71/12; A63B 71/08
USPC ................. 602/20; 128/878; 2/459, 45, 268
See application file for complete search history.

(56) References Cited

U.S. PATENT DOCUMENTS

| | | | | |
|---|---|---|---|---|
| 2,508,274 | A * | 5/1950 | Krueger | A41D 27/26 |
| | | | | 2/268 |
| 6,079,055 | A * | 6/2000 | Mencel | A41D 13/0512 |
| | | | | 2/268 |
| 6,202,214 | B1 * | 3/2001 | Light | A41D 13/0512 |
| | | | | 2/268 |
| 6,945,988 | B1 * | 9/2005 | Jones | A61F 7/10 |
| | | | | 607/108 |
| 9,936,743 | B1 * | 4/2018 | Timberlake | A41D 13/0518 |
| 2020/0146879 | A1 * | 5/2020 | Varda | A61F 7/10 |
| 2021/0236331 | A1 * | 8/2021 | Varda | A61F 7/10 |

OTHER PUBLICATIONS

The Free Dictionary by Farlex, "pocket," https://www.thefreedictionary.com/pocket.*

* cited by examiner

*Primary Examiner* — Victoria Hicks Fisher
(74) *Attorney, Agent, or Firm* — Dunlap Bennett & Ludwig PLLC

(57) ABSTRACT

A shoulder brace for patients who have lost mass in their upper torso due to a shoulder injury. The shoulder brace provides a plurality of pockets selectively placed so that when the shoulder brace is wrapped about the patient's shoulder, padding placed within the plurality of pockets mimics the look of upper body mass lost due to atrophy.

7 Claims, 3 Drawing Sheets

1

BRACE TO COVER ATROPHY IN THE SHOULDER

CROSS-REFERENCE TO RELATED APPLICATION

This application claims the benefit of priority of U.S. provisional application No. 62/975,480 filed 12 Feb. 2020, the contents of which are herein incorporated by reference.

BACKGROUND OF THE INVENTION

The present invention relates to medical devices and, more particularly, a brace to cosmetically cover atrophy in the shoulder so that the shoulder appears healthy.

There are various types of braces and casts that are used to protect a portion of a body during recovery. Medical braces are typically fitted and tightened to secure the brace about the limb. For shoulder injuries where the deltoid muscle is adversely effected, atrophy may result in significant loss of body mass. The deltoid muscle is a prominent muscle of significant mass, and in some eyes broad shoulders are a reflection of stature, especially masculine strength. Thus, loss of deltoid muscle mass may have a negative psychological impact on a patient going through rehabilitation, this is something which current shoulder braces do not address.

As can be seen, there is a need for a brace that covers an atrophied shoulder, whereby the brace gives the appearance of a healthy shoulder, thereby aiding the psychological recovery of the patient.

SUMMARY OF THE INVENTION

In one aspect of the present invention, a shoulder brace includes the following: a body having a midportion interconnecting a first flange and a second flange, defining an H-shape; the second flange extends between two ends; two first pockets are located in the second flange, each first pocket located between a midpoint of the second flange and the end; an opening of each first pocket is disposed along and just inward of a longitudinal distal edge of the second flange; and a second pocket is located in and less than coextensive of the midportion, wherein an opening to the second pocket is at an interface of the midportion and the second flange.

In another aspect of the present invention, the shoulder brace further includes the following: a second pad dimensioned to slide in and out of the second pocket opening, wherein the second pad has an oval shape with an arcuate cross section, wherein the second pocket is adapted to be adjacent an intermediate part of a deltoid muscle of a human wearer of the shoulder brace; a first pad dimensioned to slide in and out of each first pocket opening, wherein the first pad has a half-oval shape with an elongated oval cross section, wherein the two first pockets are adapted to be adjacent an anterior part and a posterior part, respectively, of said deltoid muscle of the human wearer of the shoulder brace; a strap that removable fastens and interconnects the two ends of the second flange; a body removable fastener on each end of the second flange for fastening to the strap; a removable fastener on opposing surfaces of one end of the first flange for operatively associating with each other when the shoulder brace is worn, wherein the removable fastener may be on opposing surfaces of opposing ends of the first flange for operatively associating with each other when the shoulder brace is worn, wherein a thickness of the first flange is less than a thickness of the second flange, and wherein a first width of the first flange is less than a second width of the second flange.

These and other features, aspects and advantages of the present invention will become better understood with reference to the following drawings, description and claims.

DETAILED DESCRIPTION OF THE INVENTION

Figures 1A, 1B, 1C, 2A, 2B, 2C, 2D:
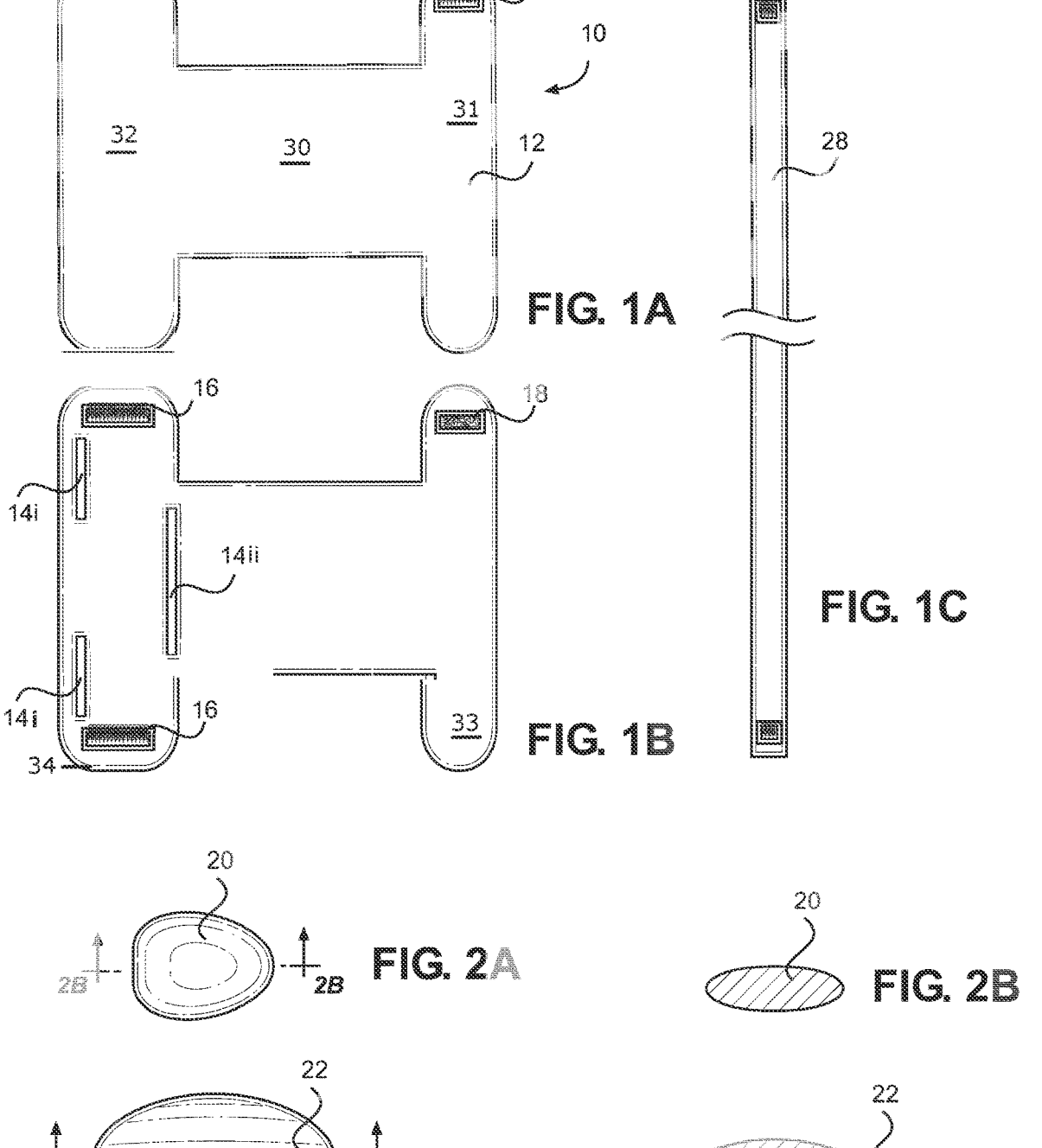
FIG. 1A is a top plan view of an exemplary embodiment of the present invention.
FIG. 1B is a bottom plan view of an exemplary embodiment of the present invention.
FIG. 1C is a top view of an exemplary embodiment of a strap of the present invention.
FIG. 2A is a top plan view of an exemplary embodiment of a first pad 20 of the present invention.
FIG. 2B is a cross-section view of the first pad 20 of the present invention, taken along line 2B-2B in FIG. 2A.
FIG. 2C is a top plan view of an exemplary embodiment of a second pad 22 of the present invention.
FIG. 2D is a cross-section view of the second pad 22 of the present invention, taken along line 2D-2D in FIG. 2C.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a shoulder brace for patients who have lost mass in their upper torso due to a shoulder injury. The shoulder brace provides a plurality of pockets selectively placed so that when the shoulder brace is wrapped about the patient's shoulder, padding placed within the plurality of pockets mimics the look of upper body mass lost due to atrophy.

Referring now to FIGS. 1A through 3C, the present invention may provide a shoulder brace 10 formed from a durable material 12, such as but not limited to natural or synthetic fabric to have an 'H'-shape. The H-shape includes a midportion 30 that interconnects two opposing flanges: a first flange 31 and a second flange 32. The first 'flange thickness' of the first flange 31 is less than the second 'flange thickness' and second flange 32.

The first flange 31 is elongated: extending along a longitudinal axis (along the vertical direction in FIG. 1B), whereby the longitudinal length is at least two times the width (along the horizontal direction in FIG. 1B). The length of the first flange 31 longitudinally extends between opposing ends 33. The top surface of the first flange 31 may have a first removable fastener 16 at one or more of the ends 33. The bottom surface of the first flange 31 has a second removable fastener 18 at one or more of the ends 33. In certain embodiments, the top and bottom surfaces have a first removable fastener 16 and a second removable fastener 18, respectively, on the same end 31. The first and second removable fasteners 16 and 18 may be hook and loop fastener or a portion thereof, or any operatively associable fastener portions for joining one object to another.

The second flange 32 is elongated: extending along a longitudinal axis (along the vertical direction in FIG. 1B), whereby the longitudinal length is at least two times the width (along the horizontal direction in FIG. 1B). The length of the second flange 32 longitudinally extends between opposing ends 34. Each end 34 of the second flange 32 has a first removable fastener 16.

The bottom surface of the second flange 32 has a plurality of pockets 14, each pocket 14 defined by an opening communicating to a cavity between the bottom surface and the top surface.

Openings of two first pockets 14i may be longitudinally disposed along and just inward of the distal longitudinal edge of the second flange 32, wherein the cavity of each first pocket 14i (and thus their opening) is disposed between a midpoint and a respective end 34, as illustrated in FIG. 1B. The opening of each first pocket 14i may be inward of the above-mentioned first removable fastener 16.

An opening to a second pocket 14ii may be longitudinally disposed at the interface between the midportion 30 and second flange 32, as illustrated in FIG. 1B. The cavity of the second pocket 14ii may extend through the midportion 30 and into the first flange 31, thus the orientation of said opening. The cavity of the second pocket 14ii may just less than coextensive with the midportion 30.

The present invention may include a first pad 20 dimensioned and adapted to slide in and out of the cavity of the first pocket 14i. Each first pad 20 may have an elongated oval cross-section and a half oval shape. The present invention also includes a second pad 22 dimensioned and adapted to be slide in and out of the cavity of the second pocket 14ii. The second pad 22 may have a bowed or arcuate cross-section and an oval shape.

The present invention also includes a strap 28, wherein the strap 28 provides removable fasteners 16 or 18 at each end thereof.

The threading and the material 12 may be woven together at regular intervals to form the shoulder brace 10 with the plurality of pockets 14 and to attach the removable fasteners 16 and 18 for securing the shoulder brace 10 around an atrophied shoulder 24 of a human user so that the padded pockets mimic the shape and look of the mass lost to atrophy-looking liked a healthy shoulder 26.

A method of using the present invention may include the following. The shoulder brace 10 disclosed above may be provided. A user may place the shoulder brace 10 on the atrophied shoulder 24 and then use the removable fasteners 16 and 18 to secure the shoulder brace 10 to their upper torso via the strap 28. Before or after securing the shoulder brace 10 to the patient, the padding 20 and 22 may be strategically placed within the shoulder brace 10 to give the appearance of a healthy shoulder.

Figures 3A, 3B:
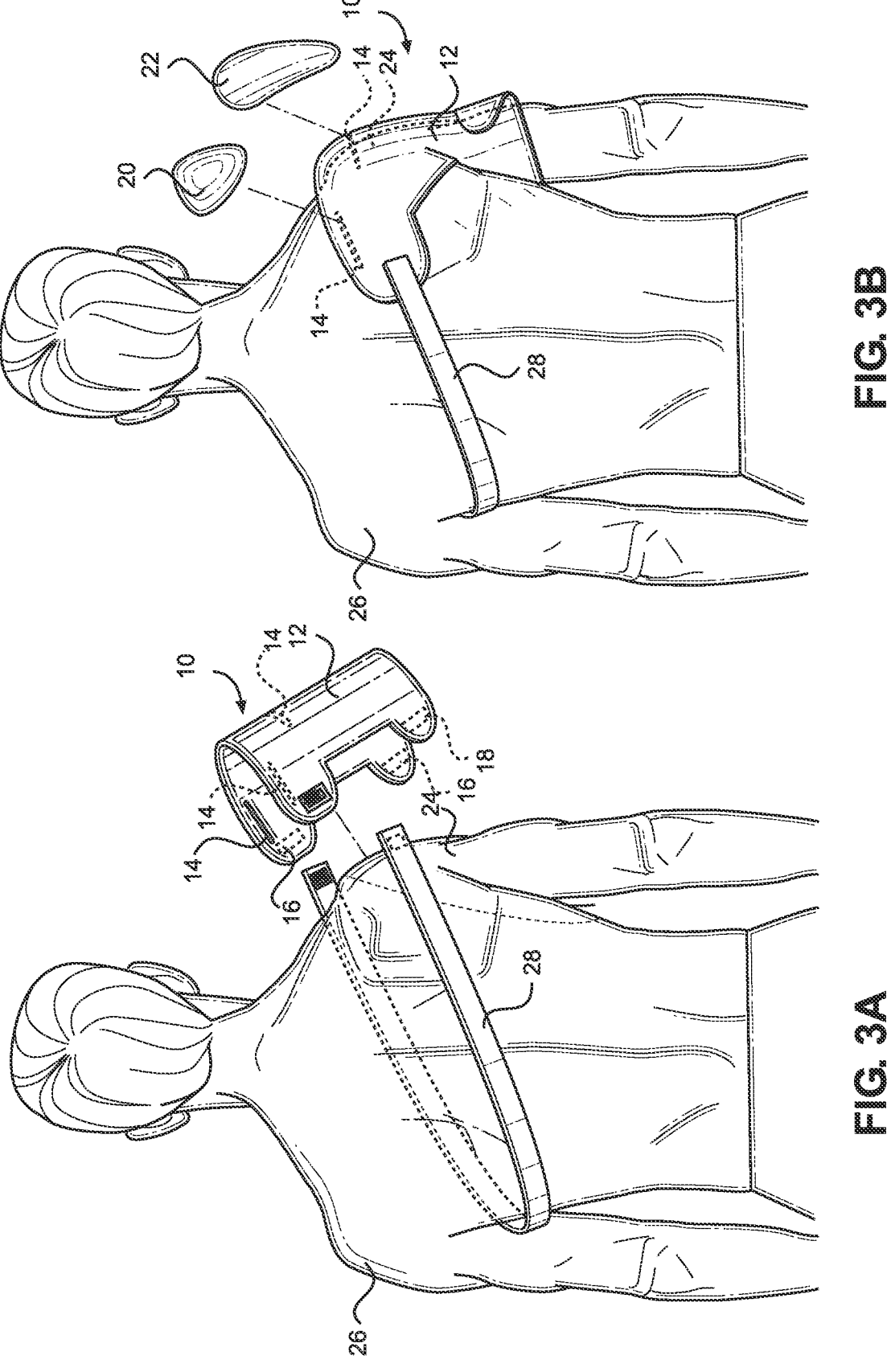
FIG. 3A is a perspective view of an exemplary embodiment step one of a method of using the present invention.
FIG. 3B is a perspective view of an exemplary embodiment step two of a method of using the present invention.
Figure 3C:
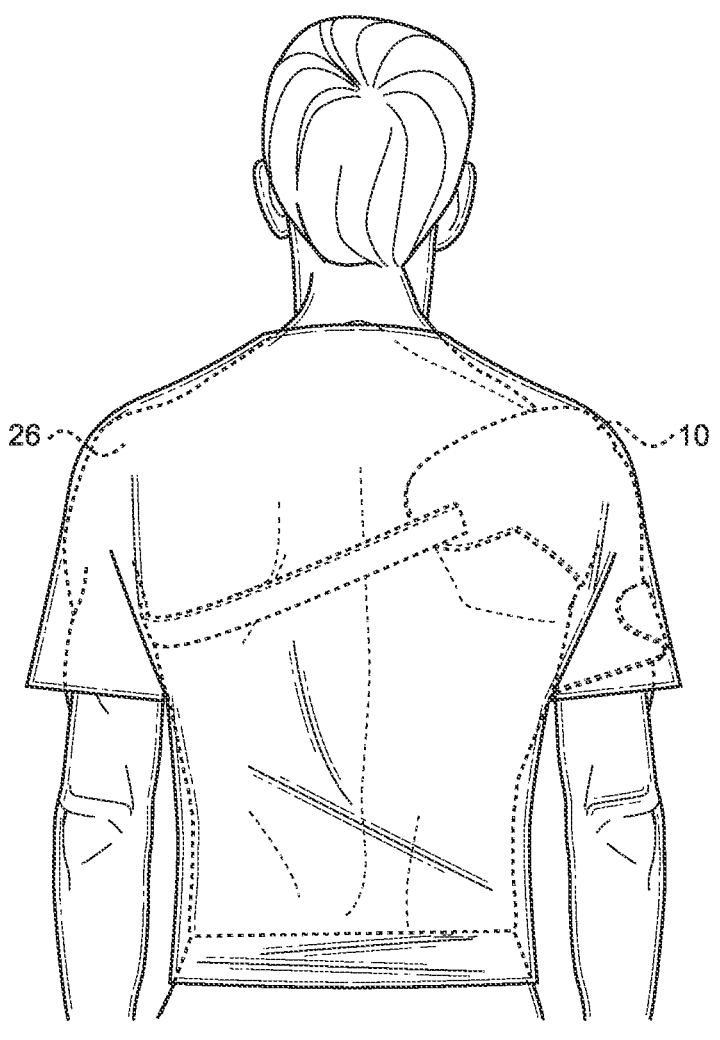
FIG. 3C is a perspective view of an exemplary embodiment step three of a method of using the present invention.

Referring to FIGS. 3A and 3B, the second pad 22 is adjacent to the intermediate part of the deltoid muscle of the human wearing the shoulder brace 10. The arcuate cross section and oval shape of the second pad 22 mimics the curved intermediate part as it starts from the top of the shoulder and depends downward. Meanwhile, the two first pads 20 are adjacent to the anterior and posterior parts, respectively, of the deltoid muscle of the human wearer. Said anterior and posterior parts tend to be flatter than the intermediate part of the deltoid and thus the elongated oval cross-sectional area and half oval shape of each of the first pads 20.

Additionally, depending on the degree of atrophy, more than one pad per pocket can be added and/or may be required.

It should be understood, of course, that the foregoing relates to exemplary embodiments of the invention and that modifications may be made without departing from the spirit and scope of the invention as set forth in the following claims.

What is claimed is:

1. A shoulder brace adapted for a human wearer having lost mass in a deltoid muscle, the shoulder brace comprising:
   a body having a midportion interconnecting a first flange and a second flange, defining an H-shape;
   the body having a bottom surface and a top surface, opposite the bottom surface;
   the second flange extends between two ends;
   two first pockets located along the bottom surface in the second flange, each first pocket located between a midpoint of the second flange and one end of said two ends, respectively, wherein the two first pockets are adapted to be adjacent to an anterior part and to a posterior part, respectively, of said deltoid muscle of the human wearer;
   for each first pocket, a first opening longitudinally extends along the bottom surface just inward of a longitudinal distal edge of the second flange so that the first opening communicates with a first cavity of the first pocket, wherein the first cavity is between the bottom surface and the top surface;
   for an anterior first pocket of the two first pockets, a first anterior deltoid-mimicking pad having an anterior shape dimensioned to be selectively slidable into the first cavity so as to define a padded anterior first pocket configured to mimic lost mass of the anterior part of said deltoid;
   for a posterior first pocket of the two first pockets, a first posterior deltoid-mimicking pad having a posterior shape dimensioned to be selectively slidable into the first cavity so as to define a padded posterior first pocket configured to mimic lost mass of the posterior part of said deltoid;
   a second pocket defined by a second cavity, wherein the second cavity is between the top surface and the bottom surface and is located in and less than coextensive of the midportion, wherein a second opening to the second pocket extends along the bottom surface at an interface of the midportion and the second flange, and wherein the second opening communicates with the second cavity; and
   a second pad having a second shape dimensioned to be selectively slidable into the second cavity so as to define a padded second pocket, wherein the padded second pocket is configured to mimic lost mass of an intermediate part of said deltoid,
   wherein each of the first anterior deltoid-mimicking pad, the first posterior deltoid-mimicking pad and the second pad are separate and distinct and have a fixed cross section,
   whereby each of the first and second openings are distinct openings relative to each other.

2. The shoulder brace of claim 1, wherein the second pad has an oval shape with an arcuate cross section.

3. The shoulder brace of claim 2, wherein the first anterior deltoid-mimicking pad and the first posterior deltoid-mimicking pad each have a half-oval shape with an elongated oval cross section.

4. The shoulder brace of claim 3, further comprising a strap that removably fastens and interconnects the two ends of the second flange.

5. The shoulder brace of claim 4, further comprising a body removable fastener on each end of the second flange for fastening to the strap.

6. The shoulder brace of claim 5, further comprising a removable fastener on opposing surfaces of opposing ends of the first flange for operatively associating with each other when the shoulder brace is worn.

7. The shoulder brace of claim 6, wherein a first width of the first flange is less than a second width of the second flange.

\* \* \* \* \*